US011521716B2

(12) United States Patent
Vianu et al.

(10) Patent No.: US 11,521,716 B2
(45) Date of Patent: Dec. 6, 2022

(54) COMPUTER-IMPLEMENTED DETECTION AND STATISTICAL ANALYSIS OF ERRORS BY HEALTHCARE PROVIDERS

(71) Applicant: Covera Health, Inc., New York, NY (US)

(72) Inventors: Ron Vianu, New York, NY (US);
Richard Herzog, New York, NY (US);
Daniel Elgort, New York, NY (US);
Robert Epstein, Belle Mead, NJ (US);
Irwin Keller, Belle Mead, NJ (US);
Murray Becker, Belle Mead, NJ (US);
John Peloquin, New York, NY (US);
Scott Schwartz, New York, NY (US);
Greg Dubbin, New York, NY (US);
Grant Langseth, New York, NY (US);
Elizabeth Sweeney, New York, NY (US); Mattia Ciollaro, Pittsburgh, PA (US); Andre Perunicic, New York, NY (US)

(73) Assignee: Covera Health, Inc., New York, NY (US)

( * ) Notice: Subject to any disclaimer, the term of this patent is extended or adjusted under 35 U.S.C. 154(b) by 860 days.

(21) Appl. No.: 16/386,006

(22) Filed: Apr. 16, 2019

(65) Prior Publication Data

US 2020/0334566 A1    Oct. 22, 2020

(51) Int. Cl.
*G16H 10/60* (2018.01)
*G06N 7/00* (2006.01)
*G16H 50/70* (2018.01)

(52) U.S. Cl.
CPC ............. *G16H 10/60* (2018.01); *G06N 7/005* (2013.01); *G16H 50/70* (2018.01)

(58) Field of Classification Search
CPC .......... G16H 10/00–80/00; G06N 3/00–99/007
See application file for complete search history.

(56) References Cited

U.S. PATENT DOCUMENTS 10,499,857 B1 * 12/2019 Nguyen ................ G06T 7/0012
10,650,929 B1 *  5/2020 Beck ...................... G16H 30/40
(Continued)

FOREIGN PATENT DOCUMENTS

KR         101477128 B1 * 12/2014 ............. G16H 10/00
WO   WO-2017151757 A1 *  9/2017
(Continued)

OTHER PUBLICATIONS

Voisin et al., "Predicting diagnostic error in radiology via eye-tracking and image analytics: Preliminary investigation in mammography," Med. Phys. 40 (10), Oct. 2013; http://dx.doi.org/10.1118/1.4820536 (Year: 2013).*

*Primary Examiner* — Jonathon A. Szumny
(74) *Attorney, Agent, or Firm* — Polsinelli, P.C.

(57) ABSTRACT

In an embodiment, a computer-implemented process comprises accessing a plurality of digitally stored, unstructured medical diagnostic data; digitally displaying a first subset of the medical diagnostic data, the first subset of the medical diagnostic data including at least a first set of diagnostic reports, using a computer display device, concurrently with digitally displaying one or more quality control checklists that are specific to a medical discipline represented in the first set of diagnostic reports; receiving digital input specifying one or more errors in the first set of diagnostic reports and digitally storing the digital input in association with the first subset of medical diagnostic data; training a hierarchical Bayesian machine learning model using the digital input and the first subset of medical diagnostic data; evaluating the hierarchical Bayesian machine learning model, after training, for a second subset of the medical diagnostic data, the (Continued)

second subset being different from the first subset, to result in outputting one or more provider error rate data; applying a grading algorithm to the one or more provider error rate data to yield one or more output provider quality score values.

27 Claims, 4 Drawing Sheets

(56) References Cited

U.S. PATENT DOCUMENTS

| | | | |
|---|---|---|---|
| 10,892,056 B2* | 1/2021 | Xie | G16H 30/40 |
| 2004/0078232 A1* | 4/2004 | Troiani | G16H 50/20 |
| | | | 705/2 |
| 2006/0190295 A1* | 8/2006 | Merkin | G16H 50/70 |
| | | | 705/2 |
| 2007/0192143 A1* | 8/2007 | Krishnan | G16H 10/20 |
| | | | 600/300 |
| 2007/0250352 A1* | 10/2007 | Tawil | G16H 10/20 |
| | | | 600/300 |
| 2009/0204436 A1* | 8/2009 | Thorne | G16H 10/60 |
| | | | 705/7.42 |
| 2014/0278448 A1* | 9/2014 | Sadeghi | G06Q 10/10 |
| | | | 705/2 |
| 2015/0033128 A1* | 1/2015 | Curd | G16H 40/40 |
| | | | 715/728 |
| 2016/0364862 A1* | 12/2016 | Reicher | G06K 9/6227 |
| 2017/0177812 A1* | 6/2017 | Sjölund | G16H 20/40 |
| 2018/0101645 A1* | 4/2018 | Sorenson | G06V 30/194 |
| 2018/0137244 A1* | 5/2018 | Sorenson | G16H 30/40 |
| 2019/0148003 A1* | 5/2019 | Van Hoe | G16H 10/60 |
| | | | 705/3 |
| 2019/0228063 A1* | 7/2019 | El-Sherif | G06Q 10/00 |
| 2020/0135326 A1* | 4/2020 | Averbach | G16H 40/20 |
| 2020/0161005 A1* | 5/2020 | Lyman | G06V 10/25 |
| 2021/0125091 A1* | 4/2021 | Fang | G06N 20/10 |

FOREIGN PATENT DOCUMENTS

| | | | | |
|---|---|---|---|---|
| WO | WO-2017152121 A1 * | 9/2017 | | G06F 16/5838 |
| WO | WO-2018011432 A1 * | 1/2018 | | G06F 19/321 |
| WO | WO-2019144116 A1 * | 7/2019 | | G06F 40/58 |

* cited by examiner

COMPUTER-IMPLEMENTED DETECTION AND STATISTICAL ANALYSIS OF ERRORS BY HEALTHCARE PROVIDERS

FIELD OF THE DISCLOSURE

One technical field of the present disclosure is computer-implemented machine learning systems that are programmed to classify digital image data alone or in combination with unstructured text data. Another technical field is computer-implemented calculation of error rates in medical diagnosis.

BACKGROUND

The approaches described in this section are approaches that could be pursued, but not necessarily approaches that have been previously conceived or pursued. Therefore, unless otherwise indicated, it should not be assumed that any of the approaches described in this section qualify as prior art merely by virtue of their inclusion in this section. Further, it should not be assumed that any of the approaches described in this section are well-understood, routine, or conventional merely by virtue of their inclusion in this section.

In present healthcare practices, digital images and written reports, the latter typically from dictation, often serve as a basis of diagnostic assessment. Radiology is one example of a field in which images of patient anatomy, and dictated records of assessment by radiologists, often serve as core records reflecting a diagnosis. However, the interpretation of digital images is often complex, requiring significant medical and anatomical knowledge as well as an ability to detect subtle or complicated patterns of information in the correct context, and therefore the radiology field has a non-zero error rate, in which patients have had their diagnostic image data interpreted incorrectly, leading to the wrong diagnosis. The result can have a significant impact on patient comfort, care patterns, treatment outcomes and costs. For example, an erroneous diagnosis could lead to preparation for or performance of a surgical procedure that is unnecessary.

Some diagnostic errors result from deficiencies in a radiologist's skill in interpreting image data, other diagnostic errors result from differences in the communication of diagnostic information in written or dictated diagnostic reports. It is commonplace for different radiology practitioners to express a diagnosis in multiple different ways in writing, or with arcane or incorrect terms; some of these variations will correctly express a patient's diagnosis and many will convey an erroneous or misleading diagnosis.

A wide variety of diagnostic errors and quality issues occur with varying prevalence rates in patient exams. Examples of categories of diagnostic errors include: (1) false positive reporting of a diagnostic finding, (2) false negative reporting of a diagnostic finding, (3) errors in which a finding is "overcalled" or graded as being overly severe, or (4) errors in which a finding is "undercalled" or graded as being too minor. Other quality issues, related to communication issues in the report, can include the following categories: (1) findings that are reported in an overly equivocal manner, (2) findings that are reported in an overly vague manner, (3) findings that are reported with inappropriate emphasis, (4) inappropriate or lack of comparisons with prior diagnostic studies, (5) inappropriate or lack of inclusion of relevant standard measures (e.g. not using the Breast Imaging Reporting and Data System or BI-RADS scoring system for mammogram reports, or (6) inappropriate or lack of follow-up recommendations. Finally, diagnostic radiology exams can also suffer from technical errors and quality issues that can include: (1) poor image quality (e.g. low signal-to-noise ratio), (2) images degraded or obscured by patient motion or other artifacts, (3) poorly configured exam protocols (e.g. an MRI exam conducted without collecting images that have a necessary image contrast setting or images collected with resolution that is too low), or (4) poor anatomical coverage of the images.

Assessing the accuracy of diagnoses and presence of specific types of errors is difficult for patients and other stakeholders, including other physicians involved in a patient's care and healthcare payers. Presently, most efforts to assess the accuracy of a diagnosis rely on obtaining a second opinion from another radiologist or medical professional and then comparing the second opinion with the first opinion. While a diagnostic accuracy assessment could be based upon favoring the second opinion of an authoritative expert, the healthcare system might not be well-served if correct diagnoses only can be achieved by a subset of experts. Furthermore, authoritative experts are themselves fallible and pathological assessment always involves a measure of subjectivity, so it may be difficult to determine if variation across the two diagnoses represent evidence of diagnostic errors present in at least one diagnosis or if the variation represents multiple ways of stating the same diagnosis. Seeking a third or multiple additional opinions on a given patient's diagnosis does not alleviate this issue and is likely prohibitive due to logistics or cost for most patients.

Therefore, there is a long-felt need in the field for a standardized, robust, and quantitative method for assessing the accuracy of patients' diagnoses and the diagnostic accuracy and error rates achieved by radiology providers. However, this requires a scalable system for standardizing multiple aspects of the diagnostic quality assessment process, including, (1) the diagnostic interpretation of image data, (2) the documentation of diagnostic findings in dictated or written diagnostic reports, and (3) the categorization of various diagnostic errors and quality issues.

While extensive medical records are usually developed for each patient in digital electronic form, typically much of the data is unstructured; examples are the digital medical images and dictated diagnostic reports, both of which are non-standardized across patient exams and not readily interpretable by machines or computers. While more structured dictation could be provided, it is an imperfect approach that is unlikely to be adopted on a widespread basis. Additional tools or systems are required to transform the unstructured information in medical images and diagnostic reports into standardized data that can be leveraged for assessment of diagnostic accuracy, error rates, and quality.

Since a multitude of diagnostic errors and related quality issues are possible in the context of most diagnostic imaging exams, it can be valuable to prioritize the specific types of diagnostic findings and diagnostic errors that a diagnostic accuracy and quality assessment system will target for evaluation. One approach to prioritization is to identify general aspects of diagnoses that are clinically meaningful for patients' care patterns and/or outcomes, and achieve high degrees of agreement between radiologist. Since perfect agreement between radiologists is not likely in any category of diagnostic finding or diagnostic error, and the levels of agreement exhibit a wide variability across categories of diagnostic findings and errors, is can be valuable for a diagnostic accuracy and quality assessment system to be able to appropriately quantify the amount of agreement that radiologists exhibit in each category of diagnostic finding and error under evaluation.

Key outputs from diagnostic accuracy and quality assessment systems include estimates of the accuracy rates and error rates that are achieved by a radiology provider under evaluation. However, if estimates of accuracy rates and error rates are directly based on data generated by independent radiologists who use a standardized process for identifying and characterizing selected diagnostic findings and diagnostic errors, the estimates will themselves not be accurate or reliable due to inter-radiologist variability.

Stakeholders in the healthcare ecosystem have developed an increased interest in quantitative and reliable healthcare quality metrics that are highly correlated with patient outcomes, patient comfort or quality of life, and costs. However, since not all diagnostic errors and quality issues have the same impact on downstream patient care patterns or patient outcomes, straightforward estimates of diagnostic accuracy rates or error rates may not represent a valuable quality metric.

When using a diagnostic accuracy and quality assessment system to evaluate multiple distinct providers, it is critical to account for the fact that different providers often care for very different patient populations. It may be inappropriate to use unadjusted estimates of diagnostic accuracy rates or error rates as standardized and generalizable measures of radiology care quality. A quality assessment system that can be used across a diverse population of providers will usually need to include some adjustment for differences between the relevant patient populations.

Furthermore, there is an acute need for computer-implemented techniques that can generate data representing the quality or accuracy of medical diagnoses in a robust and scalable manner. In some instances, institutions have attempted to replace or supplement radiologists, in the context of their clinical workflow as they perform initial interpretations of image data and generate diagnostic reports, with machine-executed image recognition and interpretation systems. These systems are programmed to inspect images and flag abnormalities. However, known systems typically identify too many false positives, or work only with abnormalities that are straightforward to find in an image, and therefore they do not add significant value to the ecosystem in this capacity.

Computer-implemented image interpretation and medical report interpretation technologies have not been developed, expanded, or adapted for use as part of a diagnostic accuracy and quality assessment system. The technical performance and design requirements for these technologies are different in this distinct application domain. In the context of an initial interpretation of image data to support (or replace) a radiologist as they generate a specific patient's diagnostic report, a computer-implemented image interpretation system will need to achieve high sensitivity, high specificity, and an ability to target a wide range of diagnostic finding types. In the context of a diagnostic accuracy and quality assessment system that is supplemented with or solely executed by a computer-implemented image interpretation system, which will also need to be integrated with a computer-implemented medical report interpretation system, there are more relaxed performance requirements with respect to sensitivity, specificity, and variety of targeted diagnostic finding types. The reason for this relaxation of performance requirements is that, as long as the sensitivity and specificity performance levels of the computer implanted systems is quantified, it is still possible calculate robust and reliable estimates of the overall diagnostic accuracy and error rates, along with appropriate confidence intervals around these estimates, that radiology providers achieve when caring for populations of patients.

SUMMARY

The appended claims may serve as a summary of the invention.

DETAILED DESCRIPTION

Figure 1:
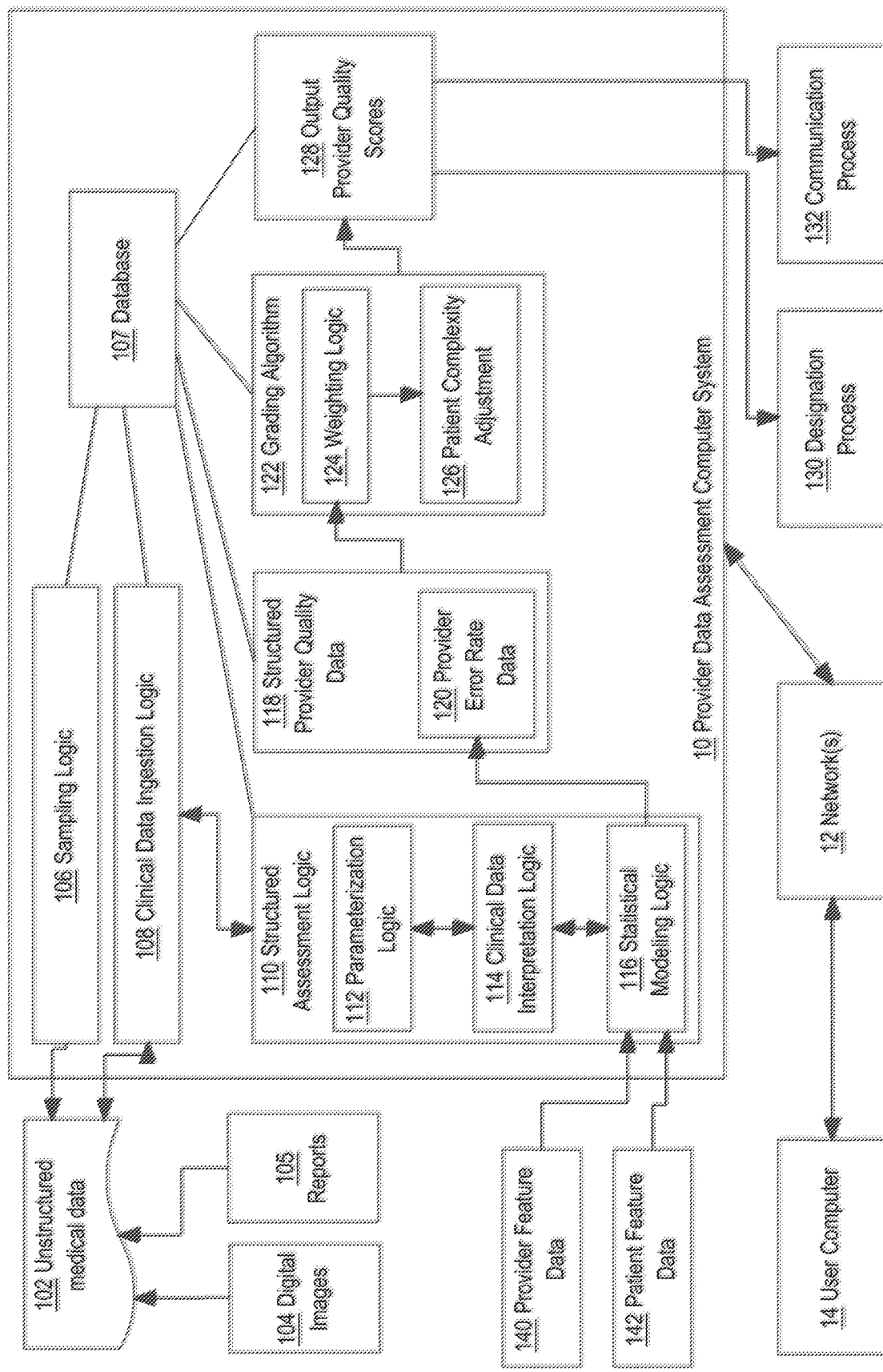
FIG. 1 illustrates an example of functional elements and data flows in a distributed computer system that may be used to implement one embodiment of provider assessment processing.

In the following description, for the purposes of explanation, numerous specific details are set forth in order to provide a thorough understanding of the present invention. It will be apparent, however, that the present invention may be practiced without these specific details. In other instances, well-known structures and devices are shown in block diagram form in order to avoid unnecessarily obscuring the present invention.

1. General Overview

In an embodiment, a system for quantifying diagnostic radiology errors uses structured and standardized exam reviews that are performed by independent radiologists to create a repository of clinically meaningful attributes of radiology images and radiology reports. Digital analysis of the attributes yields an objective truth source for any diagnosis that can be associated with digital images of anatomy or other physical features of the subject as well as an objective truth source for any diagnostic error or quality issue associated with the manner in which diagnoses were described or omitted from the radiology report.

A modified embodiment may supplement the attributes, or categories of attributes, with reliable measures of confidence or probability of correctness. These reliable measures of confidence or probability of correctness may be generated by statistical analysis of the variances across the attributes in reports that were generated by the radiologists performing structured and standardized radiology exam reviews. In some cases, the radiologists performing structured and standardized radiology exam reviews will independently review the same underlying radiology exam and generate reports that will contribute to the analysis of variance.

The techniques herein are most suitable for assessing diagnostic accuracy, errors, and/or quality related to pathology or disease that is subject to generally good agreement among experts with respect to physical features that are present, location, size and so forth.

In some embodiments, the system for quantifying diagnostic radiology errors will be optimized to generate accurate quantitative measures of diagnostic error rates and quality issues related to specific radiology providers that are selected for assessment and their associated performance with respect to specific pathologies and diseases. These quantitative measures of diagnostic error rates may be aggregated to varying levels of anatomical detail, for example: (1) a combined measure representing the rate of any error that a radiology provider makes in the context of diagnostic knee MM exams, or (2) a more narrow-scope measure representing the rate of any error that a radiology provider makes pertaining to an accurate diagnosis of meniscal tears within knee MM exams. These quantitative measures of diagnostic error rates may also be aggregated to varying levels of diagnostic error types, for example: (1) a measure representing the rate of any false positive errors that a radiology provider makes in the context of diagnostic imaging exams, or (2) a measure representing the rate of any errors in which a finding is "undercalled", or mistakenly graded as being too minor, that a radiology provider makes in the context of diagnostic imaging exams. Finally, these quantitative measures of diagnostic error rates may be aggregated to varying levels of within a radiology provider organization, for example: (1) a measure representing the rate of any diagnostic error that an individual radiologist makes in the context of selected diagnostic imaging exam types, or (2) combined measure representing the rate of any error that a group of radiologists who practice together at single radiology facility make in the context of selected diagnostic imaging exam types.

In some embodiments, the measures of diagnostic error rates will be entirely based on the empirical diagnostic error data and attributes that are produced by the independent radiologists who perform standardized reviews of the exams performed by the radiology providers under review. In some embodiments, the measures of diagnostic error rates will be based, all or in part, on statistical modeling, including hierarchical Bayesian statistical modeling, of the empirical diagnostic error data and attributes.

Some embodiments of the system for quantifying diagnostic radiology errors will also be optimized to generate measures of diagnostic quality that are modified versions of radiology provider error rates. These measures of diagnostic quality may be weighted combinations of specific diagnostic errors, such that the weighting may represent the relative likelihood that a specific type of diagnostic error will have an impact on patients' treatment pathways, clinical outcomes, or costs of treatment and subsequent care. The method for combining the various diagnostic error rates into the new quality measure may involve weighted averaging, linear or non-linear statistical modeling, or machine learning. The assignment of weights that represent the likelihood that specific types of diagnostic errors will have a clinical impact on patients may be accomplished by: (1) capturing additional data elements during the standardized diagnostic exam reviews, (2) stand-alone assessments by radiologist or other medical experts of the likely clinical impact of specific types of diagnostic errors, or (3) analysis of historical medical records of patients in combination with diagnostic error data to estimate the correlation of specific diagnostic errors or providers with specific error rates and impacts to patients' treatment patterns, costs, and outcomes.

In some embodiments, the diagnostic error data and attributes that are generated through standardized review of imaging exams will be supplemented with additional data and attributes about the radiology providers under evaluation. Examples of these supplementary data and attributes may include: (1) radiologists' educational history, including fellowship training status, (2) radiologists' years of practice, (3) radiologists' historical exam volume and case mix, (4) radiology facilities' imaging equipment, or (5) radiology facilities' imaging exam protocol configurations. This supplementary data and attributes may be leveraged by the system to: (1) generate measures of diagnostic error rates or weighted diagnostic error rates with improved accuracy, precision, or narrower confidence intervals; or (2) to generate predicted measures of diagnostic error rates or weighted diagnostic error rates for radiology providers which have not had any of their imaging exams subjected to standardized reviews and for whom only the supplementary data elements and attributes are available. The methodologies that can be employed to leverage the supplementary radiology provider data and attributes in this way involves modeling the correlations between these new supplementary data elements and the data elements related to diagnostic errors and quality issues that are generated by the standardized imaging exam reviews; the quantitative methodologies that are used in this context may include Bayesian or log-linear statistical modeling or machine learning techniques.

In some embodiments the system for quantifying diagnostic radiology errors will also be optimized to generate measures of diagnostic quality that are also adjusted for patient complexity, such that radiology providers may be penalized less for having higher rates of diagnostic errors when caring for a population of more complex patients and vice versa. To quantify the complexity of individual patients and populations of patients that are associated with the various radiology providers under evaluation, the system may leverage combination of data from: standardized reviews of imaging exams, billing or claims data, patient demographic data, or other data extracted from electronic medical records. The system may employ Bayesian or log-linear statistical modeling, linear or non-linear regression, or machine learning methodologies to achieve the patient complexity adjustment of the diagnostic quality measures.

In one embodiment, patient complexity is adjusted for using a two-step process. In step one, diagnostic error rate estimates for each radiology provider under evaluation are modeled as conditional probabilities, i.e. diagnostic errors rate for each provider are estimated conditional on the presence of specific medical conditions and severities across the patient population observed for the radiology provider. We denote the computed estimates (e.g., via regression) of these conditional probabilities as $Pr(Y|P=p)$, where Y is a variable representing diagnostic error rate and $P=p$ is a specific medical condition and severity; and we further denote the distribution of all medical conditions and severities observed for the radiology provider as $f(P=p)$, at each level of which we have the aforementioned estimated conditional probability.

In step two, a data set is defined that represents a reference patient population $f(P^*=p^*)$, which has a fixed distribution of medical conditions and severities (this distribution can be modeled using empirical observations or a reference patient population can be created with an arbitrary distribution of medical conditions and severities for this purpose). The diagnostic error rates estimated for each radiology provider, as conditional probabilities from step 1, can then be evaluated with respect to this distribution, i.e., $E[f(Y'|P=p=p^*)|f(P^*=p^*)]$ can be calculated for different providers, and these results can be directly compared to evaluate relative provider performance with respect to the same reference patient population. This two-step process allows an "apples to apples" comparison of diagnostic error rates across radiology providers that is not confounded by differences in the complexity of the patient population the radiology providers happen to be observed treating. In some embodiments the attributes generated by the standardized exam reviews are used to train computer-implemented machine learning algorithms, for example recurrent neural networks or deep learning algorithms, such that the computer-implemented algorithms can then independently analyze digital radiology images and radiology reports and automatically apply the attributes that are included in the standardized exam reviews. These computer-implemented and algorithms will be trained to analyze radiology images to identify the presence or absence and severity of the specific pathologies that are assessed by the radiologists when they perform the standardized exam reviews. When analyzing the images, the algorithms may also be trained to generate attributes that describe the technical quality of the images, for example: (1) poor image quality (e.g. low signal-to-noise ratio), (2) images degraded or obscured by patient motion or other artifacts, (3) poorly configured exam protocols (e.g. an MRI exam conducted without collecting images that have a necessary image contrast setting or images collected with resolution that is too low), or (4) poor anatomical coverage of the images. The computer-implemented and algorithms will also be trained to analyze radiology reports to identify the presence or absence of specific diagnostic findings in the reports as well as the severity of the pathologies that are reported. When analyzing the radiology reports, the algorithms may also be trained to generate additional attributes related to the quality of the report, for example: (1) findings that are reported in an overly equivocal manner, (2) findings that are reported in an overly vague manner, (3) findings that are reported with inappropriate emphasis, (4) inappropriate or lack of comparisons with prior diagnostic studies, (5) inappropriate or lack of inclusion of relevant standard measures (e.g. not using the Breast Imaging Reporting and Data System or BI-RADS scoring system for mammogram reports, or (6) inappropriate or lack of follow-up recommendations. Once the algorithm performs its assessment on the images and report associated with a specific patient exam, it will compare its assessment of the pathologies in the images with its assessment of the diagnostic findings present in the radiology report to create attributes that represent the accuracy of the radiology report and any diagnostic errors that exist.

In some embodiments, the computer-implemented algorithm will produce measures of uncertainty for each attribute it generates related to the radiology images, radiology reports, and diagnostic errors. These measures of uncertainty will be based on quantitative assessments of the computer-implemented algorithm's performance in training and validation datasets. The measures of uncertainty may also incorporate measures of the underlying variability in accuracy of the training and validation datasets themselves.

The same statistical modeling methodologies described above may be applied to the diagnostic error attributes generated by the computer-implemented algorithms, in order to calculate estimates of radiology provider diagnostic error rates and weighted measures of diagnostic error rates and diagnostic accuracy. As described above, some embodiments may supplement the diagnostic error attributes with additional attributes related to radiology provider characteristics in order to generate measures of diagnostic error rates or weighted diagnostic error rates with improved accuracy, precision, or narrower confidence intervals The analytic approaches of embodiments may execute as overnight or background processes at any time after physicians or practitioners generate new radiology images or submit new radiology reports. In some embodiments, the processes described for FIG. 1, FIG. 3 may be executed in real-time immediately after a physician submits a report to provide immediate feedback to the healthcare provider in the form of a quality review or quality report. Or, data indicating errors can be communicated to an administrator, third-party reviewer, or other system or program without direct notification to the primary physician who submitted a report. Or, in yet another alternative, errors may be scored and ranked according to seriousness or severity, and only errors above a threshold severity value may be communicated to the primary physician.

For purposes of illustrating clear examples, certain aspects of this disclosure expressly refer to use in the context of radiology practice. However, the principles of this disclosure and other embodiments may be used in connection with any other kind of healthcare practice and embodiments are not limited to radiology. Furthermore, for purposes of this disclosure, certain embodiments are described using terms having the following definitions:

Location—a region of the human body admitting specific distinct, though perhaps related, pathologies.

Pathology—a well-defined malady, for example, "central canal stenosis of the L2-3 segment in the lumbar spine".

Item—a checklist question engineered to elicit a pathology-specific diagnosis.

Diagnosis—a selected value for an item, such as None, Small, Medium, Large.

Checklist—a collection of items capturing a specific diagnosis for a particular medical discipline or specialty.

Reading provider—a physician or practitioner who is the one providing diagnoses for evaluation.

Reviewing provider—a physician or practitioner who is evaluating the diagnoses of a reading provider after the fact, for accuracy.

Practice—a group of providers that is defined by business or geographic attributes.

Provider—a broad term for a physician, other healthcare practitioner, practice, group or other aggregation.

2. Overview of Example Diagnostic Quality Assessment Framework for Radiology

FIG. 1 illustrates an example of functional elements and data flows in a distributed computer system that may be used to implement one embodiment of provider assessment processing. In an embodiment, computer-implemented processes may be programmed to support assessment of the quality level of radiology providers and practices. Other embodiments may be applied to other medical disciplines.

In one embodiment, a provider data assessment computer system 10 comprises sampling logic 106 which receives unstructured medical data 102 as input, clinical data ingestion logic 108 and structured assessment logic 110 which may receive provider feature data and patient feature data for use in executing statistical modeling operations as further described herein. These functional elements cooperate, under program control as further described functionally herein, to generate structured provider quality data 118, which may be provided as input to a grading algorithm 122 for calculation of output provider quality scores 126. The resulting scores may be provided to or used as part of a designation process 130 and/or communication process 132. A digital database 107 may be programmed to store the unstructured medical data 102 after input as well as the structured provider quality data 118, output provider quality scores 126, feature data 140, 142, and other data such as pathology prevalence data and error data for different fields of specialty.

Computer system 10 may be implemented using one or more distributed or networked computers, services, processes or other software elements hosted using desktop computers, on-premises server computers or cloud computing instances of virtual computing centers. Each of the functional elements of computer system 10 may execute as a separate asynchronous thread, service or method. In some embodiments, multiple instances of functional elements may be provided. For example, structured assessment logic 110 may execute as a plurality of independent instances in a virtualized computer to enable parallel processing of multiple datasets or parts of a single dataset. In some embodiments, aspects of structured assessment logic 110 may be programmed as a SaaS application hosted on a web server to communicate with a browser executed at a user computer 14 that is coupled to computer system 10 directly or indirectly via one or more computer networks 12 or internetworks.

One practical application of computer system 10 is detection and measurement of observed diagnostic error rates for sampling of clinical exams from radiology providers. In an embodiment, sampling logic 106 is programmed to identify which types of exams and how many clinical exams to sample from radiology providers. Exams may be represented in digital images 104, typically associated with reports 105 consisting of digitally stored text, as part of unstructured medical data 102. For example, a particular report among the reports 105 may represent a set of comments or notes on pathological structures that are visible or believed to be visible in one or more associated digital images 104. Thus, reports 105 typically represent physicians' diagnostic findings with respect to corresponding specific digital images 104, and there may be thousands or millions of sets of images and reports for different patients, exams and diagnoses. In some embodiments, sampling logic 106 is programmed to calculate a sample of exams based upon an estimated or measured prevalence of key pathologies and diagnostic errors, combined with specific criteria relating to a particular kind of designation of the provider.

For example, if the unstructured medical data 102 consists of scans of lungs, and data in database 107 indicates that lung scans have a low prevalence of lung cancer pathology as well as a low percentage of diagnostic errors for lung cancer, then the sampling logic 106 may apply a programmed rule to select a relatively high percentage, for example 50%, of all the exams for further analysis. In contrast, a different set of scans with higher pathology prevalence and/or a higher known percentage of diagnostic error might trigger a programmed rule of the sampling logic 106 to select a lower percentage, for example 10%, of all exams in the set for analysis. Furthermore, the resulting percentage or number of exams that are selected by the sampling logic 106 may be weighted or biased by other attributes and data elements in database 107 related to the provider that provided the unstructured medical data 102, for example: pre-existing quality designations or error rate estimates, the provider's patient volumes or cases mixes, or fellowship training status of providers.

In an embodiment, clinical data ingestion logic 108 is programmed to capture raw clinical data. For radiology providers, raw clinical data may comprise medical images, which could be in the form of DICOM files, and diagnostic reports, as represented by digital images 104 and reports 105. Or, digital images 104 may comprise any form of graphical images that are captured in a radiology practice including X-ray, MRI or CT images, digital film or other diagnostic data. Images 104 may be associated with corresponding reports 105, which consist of text in any digitally stored form. As previously noted, embodiments are not limited to radiology and other disciplines may interoperate with the processes herein based on raw clinical data of other types. For other providers, the type of raw clinical data may comprise electronic medical record (EMR) records or files, free-text notes, PDF files scanned from notes or generated from text files such as dictations, non-digital data such as the contents of a paper chart that has been scanned into image form or processed using optical character recognition (OCR), image-based diagnostic tests other than radiology imagery, claims data, billing data, employer-specific work data, audio files such as recordings of consultations or office visits with physicians or transcripts of the audio files, video recordings of surgeries or other interventions or procedures, or data from wearable devices. In some instances, raw clinical data may be partly structured; for example, data files may include metadata such as provider credentials, equipment attributes, length of exam, demographic or diagnostic features of patients.

It will be apparent that with datasets of the foregoing type, determining whether diagnostic errors have occurred, or other aspects of the quality of a diagnosis, cannot be obtained directly from the data. Quality attributes may relate to the technical performance of a diagnostic exam, such as poor-quality images or images that do not sufficiently cover the necessary anatomy. In an embodiment, elements of FIG. 1 are programmed to transform the unstructured raw clinical data described above into at least partly structured data, and structured review procedures and machine-executed statistical analysis are performed to analyze the available data to derive error data and quality score values. Consequently, useful and meaningful values are extracted from previously non-usable data.

In an embodiment, clinical data ingestion logic 108 is programmed to use OCR and natural language processing (NLP) techniques, which may be implemented in external code libraries or web services, to convert unstructured diagnostic report text to structured, machine-readable data. In an embodiment, clinical data ingestion logic 108 is programmed to use image processing libraries or functions to convert medical image data into structured, machine-readable data. For example, clinical data ingestion logic 108 may be programmed to perform image feature identification in digital images 104 and generate output data comprising a graph, tree or list of features that have been identified.

Other functional elements of computer system 10 are programmed to determine what diagnostic errors were made. In radiology, for example, errors could arise from low-quality images, motion artifacts from movement of the patient at the time of capturing an image, poor positioning of anatomy in relation to a camera or scanner, and so forth. In an embodiment, trained primary physicians initially prepare the raw clinical data and images, and secondary reviewers use structured processes to assess features for quality.

In an embodiment, structured assessment logic 110 is programmed with parameterization logic 112 to execute clinical data assessment parameterization. The parameterization logic 112 executes in the context of a set of one or more digital images, from among the digital images 104, that have been reviewed by a primary physician or practitioner and interpreted in a corresponding report from among the reports 105. Thus, a particular report 105 comprises a written interpretation of a set of associated images, completed by a primary physician. The parameterization logic 112 may be programmed to:

A. Select a set of one or more digital images from among the digital images 104 and a corresponding report 105, automatically according to a workflow or order, or based on input from user computer 14. The user computer 14, in this example, is associated with a secondary physician reviewer. In some embodiments, parameterization logic 112 may be programmed to present a list of available images in a graphical user interface with GUI widgets that are programmed to indicate selection of particular images.

B. Present the corresponding report via output to a computer display device of the user computer 14 and wait for user input to interpret the report.

C. Select a structured checklist, from among a plurality of structured checklists that are stored in database 107, that applies to the digital image, a medical field that is associated with the selected digital image, or that is specified in configuration data. Each checklist may be digitally stored in the database 107 as a row of a database table in which columns represent diagnostic dimensions or parameters, and then rendered in a graphical user interface in the form of a checklist under program control; thus, literal storage as a document is not required and digital data structures may be used to represent checklists in storage.

D. Render and display the structured checklist via output to a computer display device of the user computer 14 and wait for user input to respond to items in the checklist in reference to the current digital image. The secondary physician reviewer follows the checklist to detect and measure the prevalence of diagnostic errors and to control the generation of training data for artificial intelligence logic such as a neural network or classifier. The checklist addresses key diagnostic dimensions or parameters in interpretation of the digital images 104 for radiology or other specialties, customized to specific anatomical areas. Checklists may be created and stored in advance for any medical discipline and the key dimensions or parameters of quality of a checklist will reflect that discipline. For example, a checklist may prompt for input from user computer 14 to indicate (a) whether disc herniation is present in the L4-5 lumbar spine and (b) if present, whether it is small, moderate or large. Input from user computer 14 may be stored in database 107 in association with identifiers of a dataset, a particular digital image among the digital images 104, a checklist and a user account. Furthermore, for some disciplines, the use of a checklist with digital image data will not be required and checklists may be assessed based on written reports or text data, as next described.

In an embodiment, the secondary reviewer physician compares their interpretation of the digital images with the original physician's diagnostic report as abstracted by the checklist. The reviewer then uses the checklist and uses GUI widgets generated and displayed by the clinical data interpretation logic 114 to parameterize the level of agreement or disagreement between the reviewer's interpretation and the original interpretation, producing data that describes diagnostic errors. In some embodiments, clinical data interpretation logic 114 may be programmed to presume that the reviewer is correct, but some embodiments may model, under program control, variability of interpretation among reviewers, as further described.

E. Repeat the foregoing steps for all checklists applicable to the current digital image.

F. Return to the first step to process a different digital image or return control to the user computer or another system, program or process.

In this manner, computer-implemented processing may be used to cause database 107 to develop a comprehensive dataset that characterizes issues associated with a large number of digital images associated with exams. In some embodiments, each stored checklist later may be used as a portion of training data for training the statistical modeling logic 116 when implemented as a neural network or classifier. After a training phase, in an evaluation phase, the statistical modeling logic 116 may execute to receive the digital images 104, receive the reports 105, interpret the images according to one or more checklists, interpret the original physician's diagnostic report according to the checklist, compare the machine-generated interpretation of the images to the original physician's diagnostic report, utilizing the checklist to parameterize levels of agreement or disagreement, and generate output data identifying diagnostic errors with associated confidence level values. The statistical modeling logic 116 may receive provider feature data 140 and patient feature data as input to adjust the classification of images and reports, and output error data, based on variable features of providers and patients, as further described in other sections. Broadly, statistical modeling logic 116 executes as a trained classifier to detect errors in unstructured medical diagnostic data after training on similar medical diagnostic data in which errors have been explicitly identified.

One result of processing using the statistical modeling logic in this manner may be provider error date data 120, which may form one component of stored, structured provider quality data 118. In an embodiment, structured provider quality data 118 may be used in several different ways.

A. In an embodiment, the quality data 118 may be provided as input to the grading algorithm 122, which is programmed to use weighting logic 124 and patient complexity adjustment 126 to transform the error data.

In an embodiment, weighting logic 124 applies weight values to quality scores based on a combination of expert clinical input and data-drive insights about outcomes. These factors may be used to calculate weight values to assign to specific diagnostic errors, representing a weight of that error relative to its impact on later clinical care or treatment. Thus, a particular error may have a high weight value if its impact on clinical care or treatment, such as the complexity of a later treatment, patient discomfort or cost is high. Thus, a particular quality score 128 may be adjusted upward or downward based on the weight value associated with the error(s) represented in error rate data 120 that led to the score.

Patient complexity adjustment 126 is programmed to obtain data from database 107 for patient complexity including but not limited to demographic data such as age and sex, and clinical interpretation data such as number and severity of the pathologies identified in exams. Therefore, particular healthcare providers are not inappropriately credited or penalized, as part of determining quality scores 128, based on patient population dynamics. In this manner, grading algorithm 122 may be programmed to output provider quality scores 128, representing an overall quality score for a particular healthcare provider based on its error rate, the complexity of patients seen, and various features of the provider.

B. The quality scores 128 may be used in a designation process 130 to designate a particular healthcare provider using a particular label or designation from among a plurality of different labels or designations, using an ordered scale, hierarchical arrangement or other association of labels.

C. The quality scores 128 also may be provided to healthcare providers according to a structured communication process 132.

Figure 2:
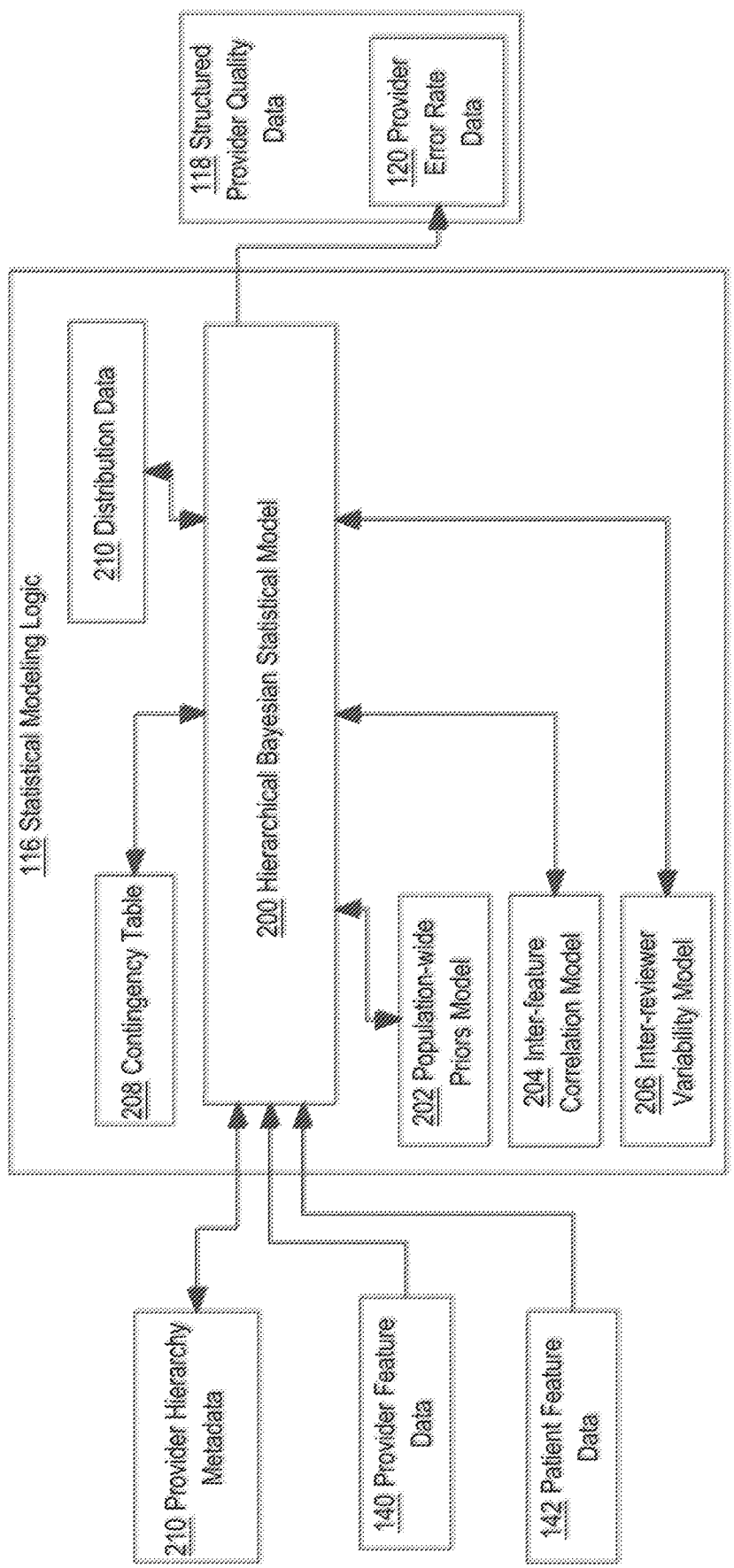
FIG. 2 illustrates further details of the statistical modeling logic of FIG. 1.
Figure 3:
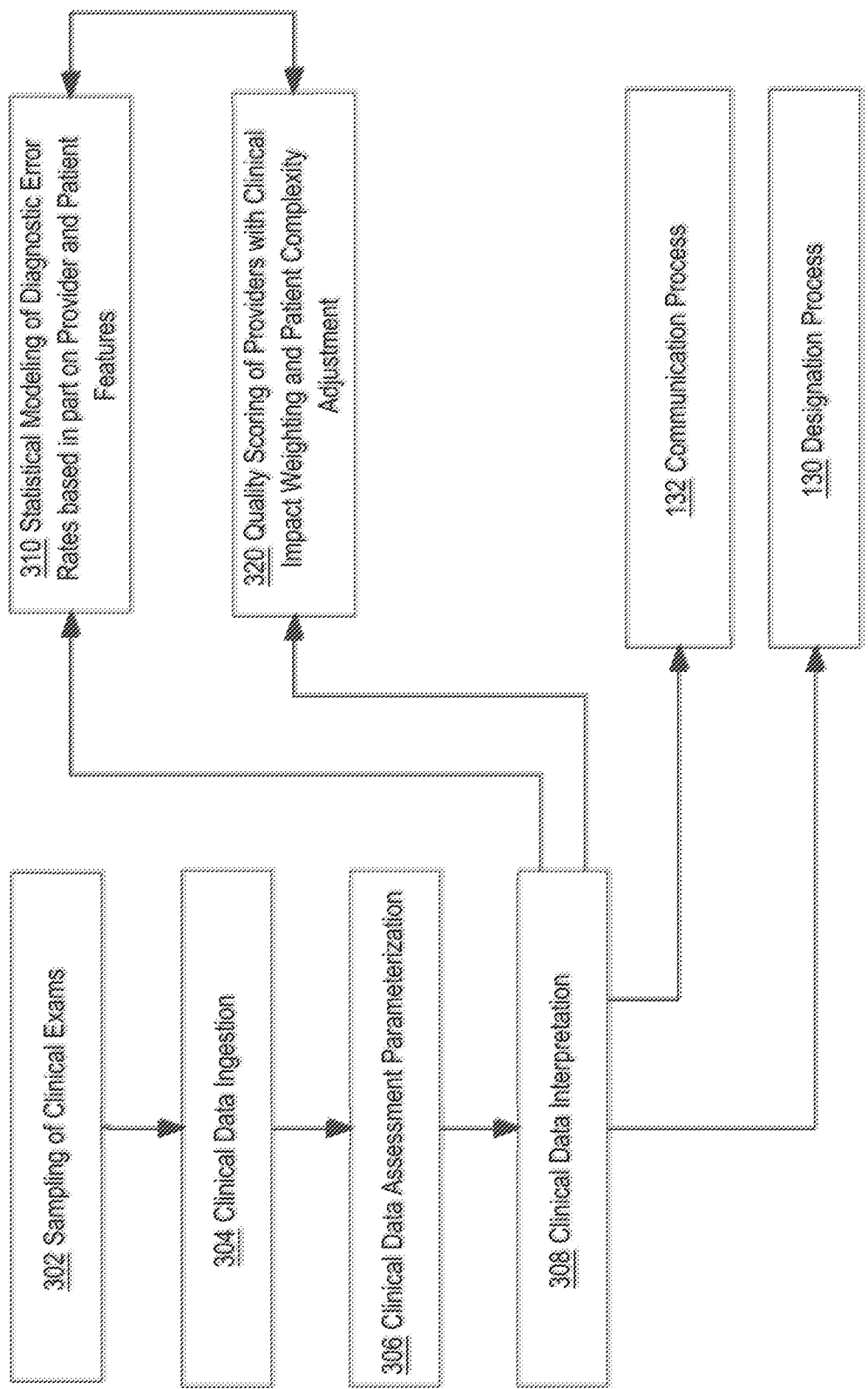
FIG. 3 illustrates an example data assessment process that may be used in an embodiment.

3. Overview of Estimating Diagnostic Error Rates Using Statistical Algorithms The system that has been generally described with reference to FIG. 1 may be used for estimating true diagnostic error rates via statistical algorithms. FIG. 2 illustrates further details of the statistical modeling logic of FIG. 1. FIG. 3 illustrates an example data assessment process that may be used in an embodiment. Referring first to FIG. 2, in one embodiment, the statistical modeling logic 116 is programmed to execute a hierarchical Bayesian statistical model 200. All elements of statistical modeling logic 116 are implemented using one or more computer programs, methods, web services, microservices and/or other software elements.

In an embodiment, foundation methodology for the statistical model 200 is to reduce outliers, narrow confidence intervals and improve the accuracy of estimates of true diagnostic error rates based on observed samples, especially for rarer types of diagnostic errors. In an embodiment, statistical model 200 uses a population-wide priors model 202, inter-feature correlation model 204 and inter-reviewer variability model 206. In an embodiment, the inter-reviewer variability model 206 is programmed to assess the reliability and consistency regarding the detection and measurement of specific types of diagnostic errors by reviewers. Its output may be used to assign confidence interval values and probability values to the provider error rate data 120 (FIG. 1). Statistical model 200 may store and use a contingency table 208 and distribution data 210 comprising one or more statistical distributions that are calculated as interim steps, as further described in this section.

In an embodiment, inter-feature correlation model 204 is programmed to use statistical techniques to characterize the correlation between groups of features. For example, groups of diagnostic error rates may be correlated; examples might be errors related to all lumbar spine pathologies, or the relationship between all diagnostic error rates of the type "overcall" to all diagnostic error rates of the type "undercall".

In an embodiment, the inter-reviewer variability model 206 is programmed to execute the seven-step process described above for parameterization logic 112, for a subset of exams consisting of associated digital images 104 and reports 105, for a plurality of different reviewers and to assess the level of agreement or disagreement of different reviewers, yielding an inter-reviewer variability score value. The inter-reviewer variability score value may be used as a factor in the statistical modeling logic 116.

In an embodiment, integration of provider feature data 140 and patient feature data 142 can further improve the estimate of true diagnostic error rates and can allow for estimates of diagnostic error rates for which the database 107 stores limited to no observed error rates. In the case of radiology, examples of features that can be represented in provider feature data 140 comprise educational history, size of practice and type of imaging equipment. Examples of features that can be represented in patient feature data 142 are age, sex, other demographic values and diagnosis.

Statistical model 200 also may receive provider hierarchy metadata 210, from database 107 for example. The provider hierarchy metadata 210 enables statistical model 200 to factor in the hierarchical structure of a healthcare provider. For example, provider hierarchy metadata 210 may specify that a particular provider is a practice, facility, individual physician or radiologist, or reflect other hierarchical levels or categories. In some embodiments, features of each entity represented in provider hierarchy metadata 210 include practice data such as size and academic affiliation; facility data such as type of imaging equipment and imaging protocols that are used; physician data such as years in practice and training attributes; and reviewer data such as years in practice and training attributes. Provider hierarchy metadata 210 may be created and stored for all the providers that are assessed using the computer system 10. The use of provider hierarchy metadata 210 enables statistical model 200 to differentiate and cross-relate features at the appropriate hierarchical level for each entity, thereby allowing for the most accurate estimate of true diagnostic error rates achieved by various practitioners.

In one embodiment, statistical model 200 is programmed to execute the following capabilities:

A. Estimation of the prevalence of diagnosis co-occurrence, via diagnosis co-occurrence statistical modeling.

B. Modeling of the agreement between reading provider and reviewer provider for a diagnosis at the item level, including: estimation of item-level diagnostic accuracy; calibration of the uncertainty of the "gold" standard diagnoses from reviewing providers using variability and inter-reviewer agreement measurements that are calculated from the data generated when multiple reviewing providers assess the same radiology exams and examples of the same pathologies and diagnostic errors.

C. Impact and significance mapping.

D. Item panel accuracy dependence.

E. Provider surveillance including modeling checklist levels and determining definitions of non-specific providers and adjustable providers.

F. Predictive extrapolation.

G. Information sharing and data pooling capabilities, including segmentation of provider populations, hierarchically informed estimation of population, and parsimonious inferential specifications.

In one embodiment, statistical model 200 is programmed to execute, using the computer system 10, functions that may be expressed for convenience in the following mathematical notation.

$$ff\left(R_{1l}, \ldots, R_{pl}, \tilde{R}_{1l}, \ldots, \tilde{R}_{pl}, D_{1l}, \ldots, D_{pl}, \theta_{1l},\right.$$
$$\left.\ldots, \theta_{pl}, \mu, \sum_{\theta} \mid X^{(R)}, X^{(\tilde{R})}, X^{(D)}\right) = f(R_{1l}, \ldots, R_{pl} \mid X^{(R)}) \times$$
$$\prod_{i=1}^{p} f(D_{il} \mid \tilde{R}_{il}, X^{(D)}, \theta_i) f(\tilde{R}_{il} \mid R_{il}, X^{(\tilde{R})}) f\left(\theta_i \mid \mu, \sum_{\theta}\right) \times f\left(\mu, \sum_{\theta}\right)$$

The expression above provides fully integrated probability characterizations of modeling specifications that are next described. Each component of the notation above represents a well-defined statistical estimation context. A Bayesian approach provides an optimized way to simultaneously address full uncertainty propagation and characterization at all data levels; incorporation of inherently unobserved measurements into the analysis; and flexible information pooling capabilities to permit identifying and representing the parsimonious dependency characteristics of the foundation data.

In an embodiment, the function $$f(R_{1l}, \ldots, R_{pl} | X^{(R)})$$

yields a log-linear contingency table represented in FIG. 2 as contingency table 208. The function provides a co-occurrence distribution of reviewing provider diagnoses $R_{1l}, \ldots R_{pl}$ for p items at location l with risk adjustment for features $X^{(R)}$.

In an embodiment, the function $$f(D_{il}|\tilde{R}_{il},X^{(D)},\theta_i)f(\tilde{R}_{il}|R_{il},X^{(\tilde{R})})$$

Provides a reading provider diagnosis distribution $D_{Il}$ for item I given uncertain true diagnosis $\tilde{R}_{Il}$ given reviewing provider diagnosis $R_{Il}$. The component expression $$f(D_{il}|\tilde{R}_{il},X^{(D)},\theta_i)$$

represents a multi-class classification conditional on unobserved $\sim R_{Il}$. Performance of $D_{Il}$ relative to $R_{Il}$ provides item-level accuracy estimation, while integration over $\sim R_{Il}$ incorporates "gold standard" uncertainty into the model. Furthermore, the component expression $$f(\tilde{R}_{il}|R_{il},X^{(\tilde{R})})$$

represents a categorical distribution capturing the observable variation in $R_{Il}$. Observable variation in $\sim R_{Il}$ is identified directly through repeated measures of multiple reviewing providers within specific checklists, as well as parametrically estimated across the population of all relevant checklists.

In an embodiment, an expert informed and healthcare impact driven score value may be derived by calculating:

$$g_k(R_{1l},D_{1l}, \ldots, R_{pl},D_{pl}|E_k,Y_k)$$

in which the function $g_k$ is defined on the basis of both expert opinion elicitation ($E_k$) and empirical evidence ($Y_k$) and aggregates accuracy portfolios into scores characterizing performance with respect to specific (k-th) financial and care outcomes In the expressions above, $\theta_i$ is a feature-driven, hierarchically informed parameter that is specific to $D_{Il}|\sim R_{Il}, X^{(D)}$. The structure and degree of dependence between $\theta_i$ (i=1, . . . p), e.g., ($\theta_1, \ldots \theta_p$) approximates $f(\mu, \Sigma_\theta)$ explicitly models and drives accuracy dependency across item panels; the specification of this form addresses appropriateness and validation of the model.

In the expressions, $X^{(D)}$ may denote a provider or features characterizing providers, which allows for non-specific provider aggregations. Particular $\theta_i$ specifications reflect $X^{(D)}$ and capture associations attributable to $X^{(D)}$ while informing estimation across I via dependency structure in $\theta_i$.

Predictive extrapolation is available through standard $X^{(D)} \theta_i$ linear form inference.

Mixture model or post-hoc subpopulation segmentation provides aggregation driven estimation. Structure and dependency across $\theta_i$ provides hierarchical information pooling and sharing. Parsimonious feature engineering in log-linear model and multi-class classification contexts addresses infeasible saturated model approaches.

Mathematical notation has been used to describe embodiments herein for conciseness and convenience, and because it is the preferred language for communication between data scientists at the level of skill contemplated by this disclosure. However, nothing in this disclosure is intended to legally claim the use of mathematical functions or notations per se, in the abstract. Instead, the mathematical notation used herein is intended as a guide for skilled data scientists or others to program one or more computer programs to realize a practical application of the concepts that have been expressed. While numerous practical applications are described in other sections, in general, programs based on the mathematical notation herein may be applied to receive digital data representing physical anatomy or pathological reports, transform or classify the data, and generate output representing error rates and scores.

Referring now to FIG. 3, in one embodiment, the foregoing processes may be implemented using a feedback-oriented process starting at block 302 at which a sampling of clinical exams is performed. Block 302 may comprise executing the functions of sampling logic 106 (FIG. 1) that have been previously described, including all alternatives and variations.

At block 304, clinical data ingestion is performed. Block 304 may comprise executing the functions of clinical data ingestion logic 108 that have been previously described, including all alternatives and variations.

At block 306, clinical data assessment parameterization is performed. Block 306 may comprise executing the operations of structured assessment logic 110 as previously described, including all alternatives and variations.

At block 308, clinical data interpretation is performed. Block 308 may involve executing the operations of clinical data interpretation logic 114 as previously described, including all alternatives and variations.

At block 310, statistical modeling of diagnostic error rates based in part on provider features and patient features is performed. Block 310 may comprise executing the operations of statistical modeling logic 116 as previously described, including all alternatives and variations.

At block 320, quality scoring of providers with clinical impact weighting and patient complexity adjustment may be performed. Block 320 may comprise using structured provider quality data 118, including provider error rate data 120, with grading algorithm 122 and the weighting and patient complexity adjustment that have been described, to yield output provider quality scores 128, as previously described, including all alternatives and variations. Furthermore, the quality scores 128 may be provided as an element of feedback to block 310 to improve training and refinement of the statistical modeling logic 116.

4. Designation of Providers Based on Quality Scoring

In an embodiment, designation process 130 (FIG. 1) may be programmed, or used manually, to create and store designations of healthcare providers based on thresholds, a hierarchy or a ranking or labeling system. In one embodiment, radiology providers may be designated as high quality providers or Centers of Excellence based on the output provider quality scores 128 that are generated for the providers. Designations may be generated based on absolute values of the quality scores 128 or based on the scores in relation to later or downstream outcomes that are observed in patient populations. In some embodiments, data for outcomes for this purpose may be obtained from medical insurance claims records.

The designation process 130 may determine designations based on criteria such as comparison of quality scores 128 to thresholds derived from national benchmark data or regional benchmark data. The benchmark data may be stored in database 107 and may be determined over time by the computer system 10, by computing quality scores 128 for a plurality of providers and storing the score values in the database in association with provider identifying data that specifies geographic location. Thereafter, the score values may be sorted and grouped by region or nation to derive mean, median or other statistically significant values for providers in a particular group, region or nation. Then, a new quality score 128 generated for a particular provider can be compared to the benchmark for a region or nation in which that particular provider is located; if the new quality score passes a threshold value corresponding to the benchmark value, then a particular designation may be created and stored, or awarded.

These techniques are expected to permit assigning a designation with a high degree of statistical confidence. In some embodiments, the processes described in section (2) and section (3) of this document may be repeated on an ongoing basis to monitor the performance of providers over time, recalculate provider error rate data 120 and regenerate output provider quality scores 128 for the same providers. Ongoing repetition and recalculation in this manner is expected to further increase confidence levels associated with scores and designations.

5. Communication Processes

In some embodiments, communication process 132 (FIG. 1) may be programmed using presentation layer logic of computer system 10 to generate performance reports or dashboards that contain applications of the information generated via section (2) and section (3). The communication of provider error rate data 120, output provider quality scores 128, designations and/or data distilled from these values is expected to induce providers to elevate the standard of care that they provide.

6. Technical Benefits

Embodiments have been described that provide data-driven, objective assessment of healthcare provider diagnoses with the benefit of generating error data and quality scores that have not been available previously.

Typically, radiology or other healthcare quality measures are based on easily accessible proxy measures of medical care quality that focus on: process or workflow (e.g. average time between stroke patient arrival at provider facility and start of stroke treatment), structure (e.g. percentage of CT exam images and reports that providers make available to unaffiliated providers for the purposes of prior study comparisons), patient safety or outcomes (e.g. death rate of patients undergoing carotid artery stenting procedures), or subjective patient satisfaction surveys (e.g. patient feedback on wait times or physician bedside manner). These approaches to radiology quality measurement do not directly assess the quality of the medical care with respect to the accuracy of the imaging exams' diagnoses and rates of diagnostic errors.

The few examples of radiology or other quality measures that do focus directly on diagnostic accuracy and diagnostic errors, require a "gold standard" secondary medical test to be available for comparison, for example, the measure of mammography exam false positive rates that is defined by the Mammography Quality Standards Act (MQSA) of 1992 requires providers to compare positive mammography exams results to subsequent results of biopsy tests. This approach to quality measurement is not generalizable to most diagnostic imaging exams and exam types because secondary diagnostic tests are not routinely performed and available for comparison with the diagnostic imaging exam report.

Some formal peer review-based quality assessment programs have been proposed for use in radiology provider organizations, for example the American College of Radiology (ACR) has proposed the "RadPeer" program in which radiologists review a sample of radiology exams performed by other radiologists in their organizations and assign a subjective summary quality score of 1a, 2a, 2b, 3a, or 3b, to indicate if the overall quality of the diagnostic imaging exam under review achieved satisfactory or unsatisfactory quality and whether any diagnostic errors that are present are likely to have a clinically significant impact on the patient. This approach to quality measurement suffers from deficiencies that include: quality scores that do generalize across provider organizations, low levels of reproducibility, and quality scores that do not include any information on rates of specific types of diagnostic errors. These subjective peer review-based methods do not systematically capture information on the levels of inter-reviewer variability associated with specific aspects of the imaging exam quality assessments, and therefore: (1) are not able to appropriately weight attributes based on the confidence that specific diagnostic errors are present, or (2) supply appropriately confidence intervals around quality measures. Further, since peer reviewed methods like these only require the reviewing radiologist to assign a single summary quality score to each exam under review, and do not generate any granular or detailed information on specific types of diagnostic errors, they are not suitable for integration with computer-implemented machine learning methods.

Unlike existing radiology quality measurement systems, the embodiments described here produce radiology quality measures that: (1) are not proxy measures of clinical care quality and instead focus directly on the quality of diagnostic imaging care (i.e. diagnostic accuracy and rates of diagnostic errors), (2) do not require a secondary diagnostic test like a biopsy to be available to serve as a "gold standard comparison", and (3) are not based on subjective summary assessments from peers within the same provider organization and instead captures quality assessment data in a structured, granular and systematic manner that allows robust and reliable quantification of diagnostic error rates and associated confidence intervals.

Finally, the framework described here, in which structured data attributes related to diagnoses and diagnostic errors are generated from each exam quality assessment review, enables: (1) the method to be scaled and supplemented using machine-implemented algorithms that are trained using the reviewer-generated attributes, and (2) for correlations between the structured data attributes and additional provider attributes to be characterized, which allows measures of diagnostic error rates or weighted diagnostic error rates to be generate with improved accuracy and precision and generated for radiology providers which have not had any of their imaging exams subjected to standardized reviews (for whom only the supplementary data elements and attributes are available).

Consequently, the techniques herein provide opportunities for peer improvement by exposing objective and detailed factors that affect quality, rather than leaving medical disciplines to operate in an environment in which practices do not know why a particular practitioner has a high or low error rate, or may be associated with patients who experience better or worse healthcare outcomes. Instead, data features exposed in the present techniques provide reliable and robust measurements of error rates. This evidence can provide reasons to improve a practice's equipment, procedures, types of exam routing or other issues.

7. Implementation Example—Hardware Overview

According to one embodiment, the techniques described herein are implemented by at least one computing device. The techniques may be implemented in whole or in part using a combination of at least one server computer and/or other computing devices that are coupled using a network, such as a packet data network. The computing devices may be hard-wired to perform the techniques, or may include digital electronic devices such as at least one application-specific integrated circuit (ASIC) or field programmable gate array (FPGA) that is persistently programmed to perform the techniques, or may include at least one general purpose hardware processor programmed to perform the techniques pursuant to program instructions in firmware, memory, other storage, or a combination. Such computing devices may also combine custom hard-wired logic, ASICs, or FPGAs with custom programming to accomplish the described techniques. The computing devices may be server computers, workstations, personal computers, portable computer systems, handheld devices, mobile computing devices, wearable devices, body mounted or implantable devices, smartphones, smart appliances, internetworking devices, autonomous or semi-autonomous devices such as robots or unmanned ground or aerial vehicles, any other electronic device that incorporates hard-wired and/or program logic to implement the described techniques, one or more virtual computing machines or instances in a data center, and/or a network of server computers and/or personal computers.

Figure 4:
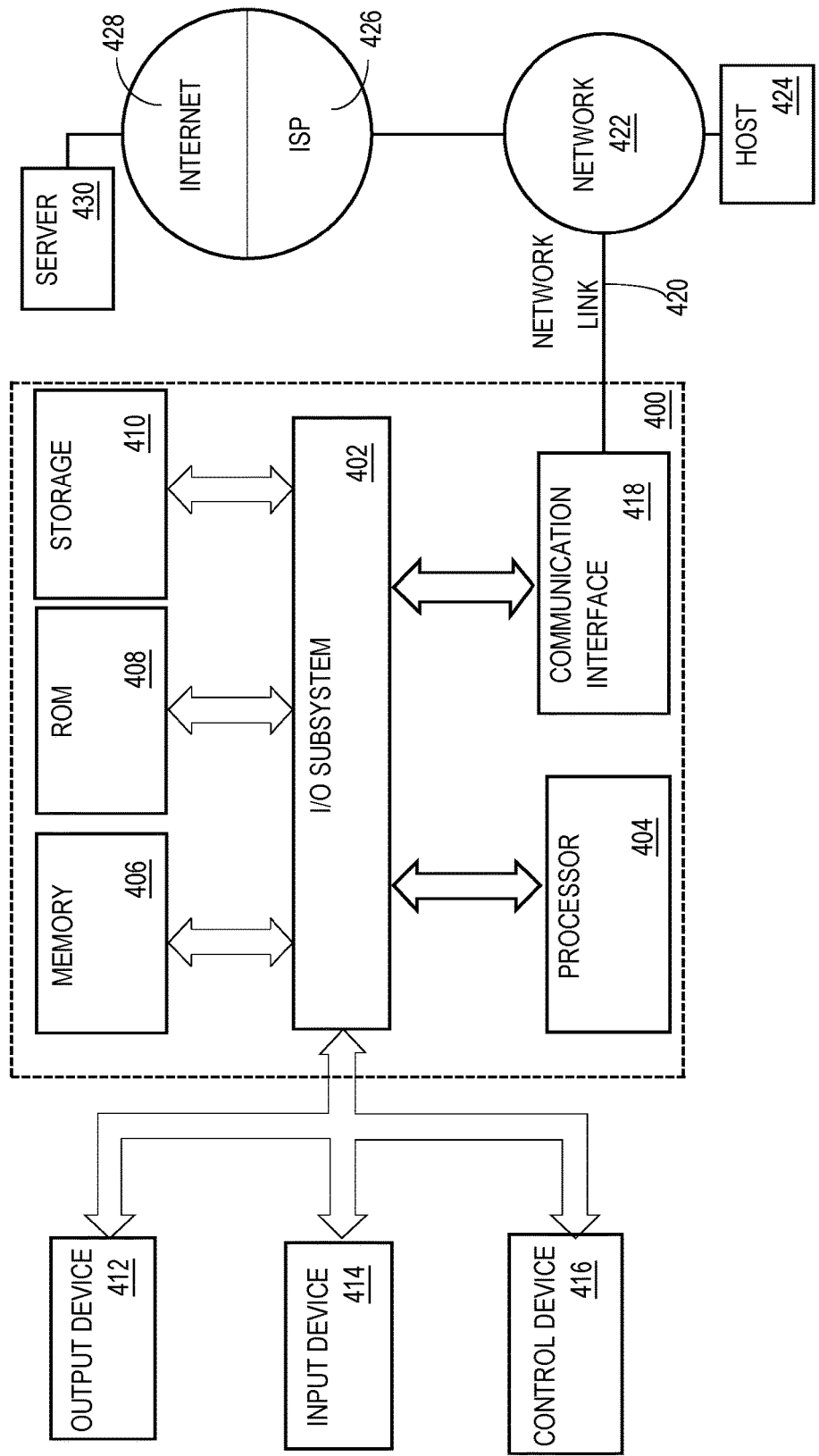
FIG. 4 illustrates an example computer system, with non-transitory computer-readable storage media, that may be used to implement all or part of the system of FIG. 1, in various embodiments.

FIG. 4 is a block diagram that illustrates an example computer system with which an embodiment may be implemented. In the example of FIG. 4, a computer system 400 and instructions for implementing the disclosed technologies in hardware, software, or a combination of hardware and software, are represented schematically, for example as boxes and circles, at the same level of detail that is commonly used by persons of ordinary skill in the art to which this disclosure pertains for communicating about computer architecture and computer systems implementations.

Computer system 400 includes an input/output (I/O) subsystem 402 which may include a bus and/or other communication mechanism(s) for communicating information and/or instructions between the components of the computer system 400 over electronic signal paths. The I/O subsystem 402 may include an I/O controller, a memory controller and at least one I/O port. The electronic signal paths are represented schematically in the drawings, for example as lines, unidirectional arrows, or bidirectional arrows.

At least one hardware processor 404 is coupled to I/O subsystem 402 for processing information and instructions. Hardware processor 404 may include, for example, a general-purpose microprocessor or microcontroller and/or a special-purpose microprocessor such as an embedded system or a graphics processing unit (GPU) or a digital signal processor or ARM processor. Processor 404 may comprise an integrated arithmetic logic unit (ALU) or may be coupled to a separate ALU.

Computer system 400 includes one or more units of memory 406, such as a main memory, which is coupled to I/O subsystem 402 for electronically digitally storing data and instructions to be executed by processor 404. Memory 406 may include volatile memory such as various forms of random-access memory (RAM) or other dynamic storage device. Memory 406 also may be used for storing temporary variables or other intermediate information during execution of instructions to be executed by processor 404. Such instructions, when stored in non-transitory computer-readable storage media accessible to processor 404, can render computer system 400 into a special-purpose machine that is customized to perform the operations specified in the instructions.

Computer system 400 further includes non-volatile memory such as read only memory (ROM) 408 or other static storage device coupled to I/O subsystem 402 for storing information and instructions for processor 404. The ROM 408 may include various forms of programmable ROM (PROM) such as erasable PROM (EPROM) or electrically erasable PROM (EEPROM). A unit of persistent storage 410 may include various forms of non-volatile RAM (NVRAM), such as FLASH memory, or solid-state storage, magnetic disk or optical disk such as CD-ROM or DVD-ROM and may be coupled to I/O subsystem 402 for storing information and instructions. Storage 410 is an example of a non-transitory computer-readable medium that may be used to store instructions and data which when executed by the processor 404 cause performing computer-implemented methods to execute the techniques herein.

The instructions in memory 406, ROM 408 or storage 410 may comprise one or more sets of instructions that are organized as modules, methods, objects, functions, routines, or calls. The instructions may be organized as one or more computer programs, operating system services, or application programs including mobile apps. The instructions may comprise an operating system and/or system software; one or more libraries to support multimedia, programming or other functions; data protocol instructions or stacks to implement TCP/IP, HTTP or other communication protocols; file format processing instructions to parse or render files coded using HTML, XML, JPEG, MPEG or PNG; user interface instructions to render or interpret commands for a graphical user interface (GUI), command-line interface or text user interface; application software such as an office suite, internet access applications, design and manufacturing applications, graphics applications, audio applications, software engineering applications, educational applications, games or miscellaneous applications. The instructions may implement a web server, web application server or web client. The instructions may be organized as a presentation layer, application layer and data storage layer such as a relational database system using structured query language (SQL) or no SQL, an object store, a graph database, a flat file system or other data storage.

Computer system 400 may be coupled via I/O subsystem 402 to at least one output device 412. In one embodiment, output device 412 is a digital computer display. Examples of a display that may be used in various embodiments include a touch screen display or a light-emitting diode (LED) display or a liquid crystal display (LCD) or an e-paper display. Computer system 400 may include other type(s) of output devices 412, alternatively or in addition to a display device. Examples of other output devices 412 include printers, ticket printers, plotters, projectors, sound cards or video cards, speakers, buzzers or piezoelectric devices or other audible devices, lamps or LED or LCD indicators, haptic devices, actuators or servos.

At least one input device 414 is coupled to I/O subsystem 402 for communicating signals, data, command selections or gestures to processor 404. Examples of input devices 414 include touch screens, microphones, still and video digital cameras, alphanumeric and other keys, keypads, keyboards, graphics tablets, image scanners, joysticks, clocks, switches, buttons, dials, slides, and/or various types of sensors such as force sensors, motion sensors, heat sensors, accelerometers, gyroscopes, and inertial measurement unit (IMU) sensors and/or various types of transceivers such as wireless, such as cellular or Wi-Fi, radio frequency (RF) or infrared (IR) transceivers and Global Positioning System (GPS) transceivers.

Another type of input device is a control device 416, which may perform cursor control or other automated control functions such as navigation in a graphical interface on a display screen, alternatively or in addition to input functions. Control device 416 may be a touchpad, a mouse, a trackball, or cursor direction keys for communicating direction information and command selections to processor 404 and for controlling cursor movement on display 412. The input device may have at least two degrees of freedom in two axes, a first axis (e.g., x) and a second axis (e.g., y), that allows the device to specify positions in a plane. Another type of input device is a wired, wireless, or optical control device such as a joystick, wand, console, steering wheel, pedal, gearshift mechanism or other type of control device. An input device 414 may include a combination of multiple different input devices, such as a video camera and a depth sensor.

In another embodiment, computer system 400 may comprise an internet of things (IoT) device in which one or more of the output device 412, input device 414, and control device 416 are omitted. Or, in such an embodiment, the input device 414 may comprise one or more cameras, motion detectors, thermometers, microphones, seismic detectors, other sensors or detectors, measurement devices or encoders and the output device 412 may comprise a special-purpose display such as a single-line LED or LCD display, one or more indicators, a display panel, a meter, a valve, a solenoid, an actuator or a servo.

When computer system 400 is a mobile computing device, input device 414 may comprise a global positioning system (GPS) receiver coupled to a GPS module that is capable of triangulating to a plurality of GPS satellites, determining and generating geo-location or position data such as latitude-longitude values for a geophysical location of the computer system 400. Output device 412 may include hardware, software, firmware and interfaces for generating position reporting packets, notifications, pulse or heartbeat signals, or other recurring data transmissions that specify a position of the computer system 400, alone or in combination with other application-specific data, directed toward host 424 or server 430.

Computer system 400 may implement the techniques described herein using customized hard-wired logic, at least one ASIC or FPGA, firmware and/or program instructions or logic which when loaded and used or executed in combination with the computer system causes or programs the computer system to operate as a special-purpose machine. According to one embodiment, the techniques herein are performed by computer system 400 in response to processor 404 executing at least one sequence of at least one instruction contained in main memory 406. Such instructions may be read into main memory 406 from another storage medium, such as storage 410. Execution of the sequences of instructions contained in main memory 406 causes processor 404 to perform the process steps described herein. In alternative embodiments, hard-wired circuitry may be used in place of or in combination with software instructions.

The term "storage media" as used herein refers to any non-transitory media that store data and/or instructions that cause a machine to operation in a specific fashion. Such storage media may comprise non-volatile media and/or volatile media. Non-volatile media includes, for example, optical or magnetic disks, such as storage 410. Volatile media includes dynamic memory, such as memory 406. Common forms of storage media include, for example, a hard disk, solid state drive, flash drive, magnetic data storage medium, any optical or physical data storage medium, memory chip, or the like.

Storage media is distinct from but may be used in conjunction with transmission media. Transmission media participates in transferring information between storage media. For example, transmission media includes coaxial cables, copper wire and fiber optics, including the wires that comprise a bus of I/O subsystem 402. Transmission media can also take the form of acoustic or light waves, such as those generated during radio-wave and infra-red data communications.

Various forms of media may be involved in carrying at least one sequence of at least one instruction to processor 404 for execution. For example, the instructions may initially be carried on a magnetic disk or solid-state drive of a remote computer. The remote computer can load the instructions into its dynamic memory and send the instructions over a communication link such as a fiber optic or coaxial cable or telephone line using a modem. A modem or router local to computer system 400 can receive the data on the communication link and convert the data to a format that can be read by computer system 400. For instance, a receiver such as a radio frequency antenna or an infrared detector can receive the data carried in a wireless or optical signal and appropriate circuitry can provide the data to I/O subsystem 402 such as place the data on a bus. I/O subsystem 402 carries the data to memory 406, from which processor 404 retrieves and executes the instructions. The instructions received by memory 406 may optionally be stored on storage 410 either before or after execution by processor 404.

Computer system 400 also includes a communication interface 418 coupled to bus 402. Communication interface 418 provides a two-way data communication coupling to network link(s) 420 that are directly or indirectly connected to at least one communication networks, such as a network 422 or a public or private cloud on the Internet. For example, communication interface 418 may be an Ethernet networking interface, integrated-services digital network (ISDN) card, cable modem, satellite modem, or a modem to provide a data communication connection to a corresponding type of communications line, for example an Ethernet cable or a metal cable of any kind or a fiber-optic line or a telephone line. Network 422 broadly represents a local area network (LAN), wide-area network (WAN), campus network, internetwork or any combination thereof. Communication interface 418 may comprise a LAN card to provide a data communication connection to a compatible LAN, or a cellular radiotelephone interface that is wired to send or receive cellular data according to cellular radiotelephone wireless networking standards, or a satellite radio interface that is wired to send or receive digital data according to satellite wireless networking standards. In any such implementation, communication interface 418 sends and receives electrical, electromagnetic or optical signals over signal paths that carry digital data streams representing various types of information.

Network link 420 typically provides electrical, electromagnetic, or optical data communication directly or through at least one network to other data devices, using, for example, satellite, cellular, Wi-Fi, or BLUETOOTH technology. For example, network link 420 may provide a connection through a network 422 to a host computer 424.

Furthermore, network link 420 may provide a connection through network 422 or to other computing devices via internetworking devices and/or computers that are operated by an Internet Service Provider (ISP) 426. ISP 426 provides data communication services through a world-wide packet data communication network represented as internet 428. A server computer 430 may be coupled to internet 428. Server 430 broadly represents any computer, data center, virtual machine or virtual computing instance with or without a hypervisor, or computer executing a containerized program system such as DOCKER or KUBERNETES. Server 430 may represent an electronic digital service that is implemented using more than one computer or instance and that is accessed and used by transmitting web services requests, uniform resource locator (URL) strings with parameters in HTTP payloads, API calls, app services calls, or other service calls. Computer system 400 and server 430 may form elements of a distributed computing system that includes other computers, a processing cluster, server farm or other organization of computers that cooperate to perform tasks or execute applications or services. Server 430 may comprise one or more sets of instructions that are organized as modules, methods, objects, functions, routines, or calls. The instructions may be organized as one or more computer programs, operating system services, or application programs including mobile apps. The instructions may comprise an operating system and/or system software; one or more libraries to support multimedia, programming or other functions; data protocol instructions or stacks to implement TCP/IP, HTTP or other communication protocols; file format processing instructions to parse or render files coded using HTML, XML, JPEG, MPEG or PNG; user interface instructions to render or interpret commands for a graphical user interface (GUI), command-line interface or text user interface; application software such as an office suite, internet access applications, design and manufacturing applications, graphics applications, audio applications, software engineering applications, educational applications, games or miscellaneous applications. Server 430 may comprise a web application server that hosts a presentation layer, application layer and data storage layer such as a relational database system using structured query language (SQL) or no SQL, an object store, a graph database, a flat file system or other data storage.

Computer system 400 can send messages and receive data and instructions, including program code, through the network(s), network link 420 and communication interface 418. In the Internet example, a server 430 might transmit a requested code for an application program through Internet 428, ISP 426, local network 422 and communication interface 418. The received code may be executed by processor 404 as it is received, and/or stored in storage 410, or other non-volatile storage for later execution.

The execution of instructions as described in this section may implement a process in the form of an instance of a computer program that is being executed, and consisting of program code and its current activity. Depending on the operating system (OS), a process may be made up of multiple threads of execution that execute instructions concurrently. In this context, a computer program is a passive collection of instructions, while a process may be the actual execution of those instructions. Several processes may be associated with the same program; for example, opening up several instances of the same program often means more than one process is being executed. Multitasking may be implemented to allow multiple processes to share processor 404. While each processor 404 or core of the processor executes a single task at a time, computer system 400 may be programmed to implement multitasking to allow each processor to switch between tasks that are being executed without having to wait for each task to finish. In an embodiment, switches may be performed when tasks perform input/output operations, when a task indicates that it can be switched, or on hardware interrupts. Time-sharing may be implemented to allow fast response for interactive user applications by rapidly performing context switches to provide the appearance of concurrent execution of multiple processes simultaneously. In an embodiment, for security and reliability, an operating system may prevent direct communication between independent processes, providing strictly mediated and controlled inter-process communication functionality.

The term "cloud computing" is generally used herein to describe a computing model which enables on-demand access to a shared pool of computing resources, such as computer networks, servers, software applications, and services, and which allows for rapid provisioning and release of resources with minimal management effort or service provider interaction.

A cloud computing environment (sometimes referred to as a cloud environment, or a cloud) can be implemented in a variety of different ways to best suit different requirements. For example, in a public cloud environment, the underlying computing infrastructure is owned by an organization that makes its cloud services available to other organizations or to the general public. In contrast, a private cloud environment is generally intended solely for use by, or within, a single organization. A community cloud is intended to be shared by several organizations within a community; while a hybrid cloud comprises two or more types of cloud (e.g., private, community, or public) that are bound together by data and application portability.

Generally, a cloud computing model enables some of those responsibilities which previously may have been provided by an organization's own information technology department, to instead be delivered as service layers within a cloud environment, for use by consumers (either within or external to the organization, according to the cloud's public/private nature). Depending on the particular implementation, the precise definition of components or features provided by or within each cloud service layer can vary, but common examples include: Software as a Service (SaaS), in which consumers use software applications that are running upon a cloud infrastructure, while a SaaS provider manages or controls the underlying cloud infrastructure and applications. Platform as a Service (PaaS), in which consumers can use software programming languages and development tools supported by a PaaS provider to develop, deploy, and otherwise control their own applications, while the PaaS provider manages or controls other aspects of the cloud environment (i.e., everything below the run-time execution environment). Infrastructure as a Service (IaaS), in which consumers can deploy and run arbitrary software applications, and/or provision processing, storage, networks, and other fundamental computing resources, while an IaaS provider manages or controls the underlying physical cloud infrastructure (i.e., everything below the operating system layer). Database as a Service (DBaaS) in which consumers use a database server or Database Management System that is running upon a cloud infrastructure, while a DbaaS provider manages or controls the underlying cloud infrastructure, applications, and servers, including one or more database servers.

In the foregoing specification, embodiments of the invention have been described with reference to numerous specific details that may vary from implementation to implementation. The specification and drawings are, accordingly, to be regarded in an illustrative rather than a restrictive sense. The sole and exclusive indicator of the scope of the invention, and what is intended by the applicants to be the scope of the invention, is the literal and equivalent scope of the set of claims that issue from this application, in the specific form in which such claims issue, including any subsequent correction.

What is claimed is:

1. A computer-implemented method comprising:
   accessing a plurality of digitally stored, unstructured medical diagnostic data;
   digitally displaying a first subset of the medical diagnostic data, the first subset of the medical diagnostic data including at least a first set of diagnostic reports, using a computer display device, concurrently with digitally displaying one or more quality control checklists that are specific to a medical discipline represented in the first set of diagnostic reports;
   receiving digital input specifying one or more errors in the first set of diagnostic reports and digitally storing the digital input in association with the first subset of medical diagnostic data;
   training a hierarchical Bayesian machine learning model in one or more training phases using the digital input as labels for training data comprising at least the first subset of medical diagnostic data, wherein the hierarchical Bayesian machine learning model:
      is trained on provider hierarchy metadata; and
      integrates a population-wide priors model, an inter-feature correlation model and an inter-reviewer variability model;
   after completing the one or more training phases, performing an evaluation phase using the hierarchical Bayesian machine learning model to generate one or more provider error rate data, wherein the hierarchical Bayesian machine learning model generates the one or more provider error rate data based on an input comprising a second subset of the medical diagnostic data, the second subset being different from the first subset;
   applying a grading algorithm to the one or more provider error rate data to yield one or more output provider quality score values;
   wherein the method is performed by one or more computing devices.

2. The method of claim 1, further comprising training the hierarchical Bayesian machine learning model at least in part using provider feature data and patient feature data.

3. The method of claim 1, further comprising applying the grading algorithm to the one or more provider error rate data to yield one or more initial provider quality score values, modifying the initial provider quality score values by applying a provider weight value associated with a particular healthcare provider, again modifying the initial provider quality score values by applying a patient complexity adjustment value, to transform the initial provider quality score values into the one or more output provider quality score values.

4. The method of claim 3, the provider weight value comprising a provider-specific clinical impact weighting factor.

5. The method of claim 1, the unstructured medical diagnostic data comprising a plurality of Digital Imaging and Communications in Medicine (DICOM) digital images of patient anatomy and a corresponding plurality of radiology diagnostic reports that are based on the images.

6. The method of claim 1, the accessing comprising determining a provider identity value that uniquely identifies a particular healthcare provider; based on the provider identity value, retrieving a sampling factor for the particular healthcare provider from a database;
   sampling the first subset of the medical diagnostic data from all the medical diagnostic data based upon the sampling factor.

7. A computer-implemented method comprising:
   from among a plurality of digitally stored records of diagnostic imaging examinations, selecting a first subset of records of diagnostic imaging examinations that are associated with a set of healthcare providers under assessment for structured exam quality review;
   accessing a first subset of digitally stored, unstructured medical diagnostic data associated with the first subset of records, the first subset of medical diagnostic data including at least a first set of diagnostic reports;
   conducting the structured exam quality review by digitally displaying the first subset of medical diagnostic data including at least the first set of diagnostic reports, using a computer display device, concurrently with digitally displaying one or more structured quality control checklists that are specific to a medical discipline and representing diagnostic dimensions or parameters of quality represented in the first set of diagnostic reports;
   receiving digital input, via the one or more checklists, specifying one or more error attribute values representing attributes of errors in the first set of diagnostic reports and digitally storing the digital input in association with the first subset of medical diagnostic data and one or more identifiers corresponding to the one or more checklists, wherein each error attribute value represents a level of agreement or disagreement between an interpretation of a diagnostic imaging examination of the first subset of records of diagnostic imaging examinations by a healthcare provider of the set of healthcare providers under assessment and an interpretation of the diagnostic imaging examination of the first subset of records of diagnostic imaging examinations by a reviewer;
   training a hierarchical Bayesian machine learning model in one or more training phases using the digital input as labels for training data comprising at least the first subset of medical diagnostic data for estimating rates of diagnostic errors committed by each healthcare provider under evaluation, the healthcare providers each comprising an individual radiologist or group of radiologists practicing together at a facility, facilities, or affiliated with a common provider organization;
   after completing the one or more training phases, performing an evaluation phase using the hierarchical Bayesian machine learning model to generate one or more provider error rate data, wherein the hierarchical Bayesian machine learning model generates the one or more provider error rate data based on an input comprising a second subset of the medical diagnostic data, the second subset of medical diagnostic data including at least a second set of diagnostic reports different from the first set of diagnostic reports included in the first subset of medical diagnostic data;

applying a grading algorithm to the one or more provider error rate data to yield one or more output provider quality score values;

wherein the method is performed by one or more computing devices.

8. The method of claim 7, further comprising determining one or more correlations and qualitative relationships between the error attribute values generated by the structured exam quality reviews, estimates of provider error rates, and additional provider attributes.

9. The method of claim 8, further comprising using the one or more correlations and qualitative relationships to perform one of: generating measures of diagnostic error rates or weighted diagnostic error rates with improved accuracy, precision, or narrower confidence intervals; generating predicted measures of diagnostic error rates or weighted diagnostic error rates for radiology providers which have not had any of their imaging exams subjected to the structured exam quality reviews and for whom only supplementary data elements and additional provider attribute values are available.

10. The method of claim 7, the rates of diagnostic errors being related to an aggregated set of diagnostic errors or subsets of diagnostic errors defined by one or more of a relationship to a common anatomical structure or structures.

11. The method of claim 7, the rates of diagnostic errors being related to a type of diagnostic error selected from among false positive, false negative, overcall, or undercall.

12. The method of claim 7, the rates of diagnostic errors being related to a level of severity of clinical impact to patients' care or outcomes.

13. The method of claim 7, the rates of diagnostic errors being related to a level of egregiousness of a specific diagnostic error with respect to an estimated difficulty of making a correct diagnosis.

14. The method of claim 7, further comprising generating one or more benchmarks and quality thresholds for use in assigning designations and categorizations to providers based on their assessed quality performance levels.

15. The method of claim 7, further comprising generating one or more reports of the provider error rate data or provider quality score values.

16. The method of claim 7, further comprising digitally displaying the one or more structured checklists with a plurality of checklist input fields that are programmed to receive one or more of: (1) a presence and severity of specific pathologies or anatomical abnormalities that are present in medical images, (2) an inclusion of specific diagnostic findings in medical reports, (3) a presence of specific technical quality issues in the medical images and reports, (4) a presence of specific diagnostic errors in the medical reports, (5) and assessment of a likelihood of present diagnostic errors and technical quality issues causing a clinically important impact on a patient.

17. The method of claim 7, the selecting further comprising automatically determining a number and a set of types of diagnostic imaging exams to review from each provider.

18. The method of claim 7, the selecting further comprising weighting the selecting based upon magnitudes of one or more provider attribute values selected from among provider practice size, patient mix, and provider training profiles.

19. The method of claim 7, the selecting further comprising randomly sampling from among the plurality of digitally stored records of diagnostic imaging examinations to select the first subset of records of diagnostic imaging exams for the structured exam quality review.

20. The method of claim 7, the selecting further comprising selecting a subset of exam records for multiple independent structured exam quality reviews, and in response, repeating, via two or more iterations, the step of receiving digital input, via the checklists, specifying one or more errors in the first set of diagnostic reports and digitally storing the digital input in association with the first subset of medical diagnostic data, in which each iteration comprises receiving different digital input from a different computer.

21. The method of claim 7, the machine learning algorithm being programmed to generate estimated values of confidence intervals associated with each provider diagnostic error rate value.

22. The method of claim 17, the machine learning algorithm being programmed to analyze data from exam records that have been subjected to multiple independent instances of the structured exam quality review to produce improved estimates of confidence intervals associated with each provider error rate value.

23. The method of claim 7, the rates of diagnostic errors comprising weighted combinations of category rates of one or more of relationship to a common anatomical structure or structures, relationship to a type of diagnostic error selected from among false positive, false negative, overcall, or undercall, or relationship to a level of severity or egregiousness selected from among large overcall or small overcall.

24. The method of claim 23, wherein weight values of the category rates represent likelihoods that specific diagnostic errors will have a clinically important impact on the patient.

25. The method of claim 24, the weight values of the category rates being generated based on additional data elements during the structured exam quality reviews, standalone assessments by radiologists or other medical experts of a likely clinical impact of specific types of diagnostic errors, or analysis of historical medical records of patients in combination with diagnostic error data to estimate the correlation of specific diagnostic errors or providers with specific error rates and impacts to patients' treatment patterns, costs, and outcomes.

26. The method of claim 25, further comprising adjusting the rates of diagnostic errors or the weight values based on an estimated measure of patient complexity of a patient population associated with each healthcare provider undergoing the structured exam quality review.

27. The method of claim 7, further comprising automatically machine generating synthetic error attribute values based on one or more of medical images, medical reports, and/or combinations of medical images and reports, the machine generating being trained using the error attribute values that were generated as part of conducting the structured exam quality review.

* * * * *